US012311105B2

United States Patent
Chase et al.

(10) Patent No.: US 12,311,105 B2
(45) Date of Patent: May 27, 2025

(54) METHOD AND APPARATUS TO GUIDE MECHANICAL VENTILATION

(71) Applicant: TIRO Medical Limited, Christchurch (NZ)

(72) Inventors: James Geoffrey Chase, Christchurch (NZ); Cong Zhou, Shanghai (CN)

(73) Assignee: Tiro Medical Limited, Christchurch (NZ)

( * ) Notice: Subject to any disclaimer, the term of this patent is extended or adjusted under 35 U.S.C. 154(b) by 776 days.

(21) Appl. No.: 17/539,519

(22) Filed: Dec. 1, 2021

(65) Prior Publication Data
US 2022/0168527 A1 Jun. 2, 2022

Related U.S. Application Data

(60) Provisional application No. 63/120,261, filed on Dec. 2, 2020.

(51) Int. Cl.
*A61M 16/00* (2006.01)
*G16H 20/40* (2018.01)
*G16H 40/63* (2018.01)

(52) U.S. Cl.
CPC ...... *A61M 16/026* (2017.08); *A61M 16/0003* (2014.02); *G16H 20/40* (2018.01); *G16H 40/63* (2018.01); *A61M 2016/0027* (2013.01); *A61M 2016/0039* (2013.01); *A61M 2205/3379* (2013.01); *A61M 2230/46* (2013.01)

(58) Field of Classification Search
CPC .............. A61M 16/00; A61M 16/0003; A61M 16/0006; A61M 16/0009; A61M 16/0012; A61M 16/021; A61M 16/022; A61M 16/024; A61M 16/026; A61M 2230/46; A61M 2016/0015–0042; G16H 20/00; G16H 20/40; G16H 40/40; G16H 40/63; G16H 50/50
See application file for complete search history.

(56) References Cited

U.S. PATENT DOCUMENTS

2014/0373845 A1* 12/2014 Dong ................. A61M 16/026
128/204.23
2020/0327993 A1* 10/2020 Karbing ............ A61M 16/0003

OTHER PUBLICATIONS

Chiew et al. "Model-based PEEP optimisation in mechanical ventilation" (Year: 2011).*
Morton et al. "Predictive Virtual Patient Modelling of Mechanical Ventilation: Impact of Recruitment Function" (Year: 2019).*
Morton et al. "A virtual patient model for mechanical ventilation" (Year: 2018).*

* cited by examiner

*Primary Examiner* — Rachel T Sippel
*Assistant Examiner* — Gwynneth L Howell
(74) *Attorney, Agent, or Firm* — Bond, Schoeneck & King, PLLC; Joseph M. Noto

(57) ABSTRACT

A method and device for developing an automated digital cloning method to create an accurate, predictive and personalized virtual patient model enabling personalized precision mechanical ventilation care.

13 Claims, 16 Drawing Sheets

METHOD AND APPARATUS TO GUIDE MECHANICAL VENTILATION

CROSS REFERENCE

This application claims the benefit of the filing date of U.S. Provisional Patent Application No. 63/120,261, filed Dec. 2, 2020, which is hereby incorporated by reference in its entirety.

FIELD

The present invention relates to a method and apparatus to guide mechanical ventilation of a patient in the treatment of respiratory ailments.

BACKGROUND

Mechanical ventilation (MV) is a core therapy for respiratory failure and acute respiratory distress syndrome (ARDS) patients in the intensive care unit (ICU). It is particularly important in treating Covid-19 patients. However, non-optimal MV settings can cause ventilator induced lung injury (VILI) and increase length of stay, mortality, and cost.

During ventilation, titration of positive end-expiratory pressure (PEEP) is one preferred way to keep alveoli open and improve oxygenation. However, determining the optimal PEEP for an individual patient is still unclear in clinical practice. Specifically, lung protective strategies using a tidal volume of 6-8 mL/kg predicted body weight (PBW) and a plateau pressure lower than 30 cm $H_2O$ are well accepted. More recent studies suggest there might not be a constant safe plateau pressure over time as patient condition varies, and airway pressure should thus be minimised where possible. However, the means of determining the best or safest PEEP and other ventilator settings to provide care within these current guidelines are not known.

While using lower tidal volumes and peak pressures is a safer lung-protective strategy, sufficient PEEP is needed to provide alveolar recruitment and adequate gas exchange. In addition, clinical evidence has reported both lower and/or higher PEEP ventilation reduce mortality in different subgroup analyses, confusing the choices. It is clear optimal MV settings, particularly PEEP, have significant inter- and intra-individual variability, especially over time as condition varies, requiring the ability to accurately monitor, capture, and predict lung response to MV settings to guide care at a level that current care, protocols, and equipment cannot provide.

Finally, there is the risk of asynchrony, where the patient spontaneously breathes and is out of synchronisation with the ventilator, distorting the pressure and flow waveforms from what the ventilator was set to deliver. Asynchrony can occur in fully supported MV, as well as during assisted spontaneous breathing (ASB) MV modes, such as the commonly used pressure support and Bi-PAP ventilation modes, where a mismatch can occur between patient-driven and ventilator action. Asynchrony is thus common and comes in many forms. Importantly, clinical data demonstrates patient SB effort can cause up to 85% asynchrony rate, associated with failure of MV weaning and longer length of stay with its higher cost.

Statistical and machine learning/artificial intelligence-based models are efficient in interpreting large amounts of data to provide a best mathematical combination for predictive relationships but offer poor to no understanding of the underlying mechanics, even if acceptable prediction of response is obtained. A computational or computer model of the underlying mechanics offers more explicit meaning, physically and physiologically, and is thus more suitable for building a virtual patient model. However, such deterministic models can suffer either too great a complexity to identify or too great a simplicity for accurate use.

Current studies of basis-function based virtual patient lung mechanics models have shown accurate modelling and prediction based on a well-validated single compartment linear lung model. These models assume the shape of changes in lung elastance and resistance over pressure, volume, and flow, and identify the specific details of that shape from measured breathing data (pressure, flow, volume). However, they lack precision in fully representing lung mechanics, such as the additional lung volume or dynamic functional residual capacity ($V_{frc}$) obtained when changing PEEP, which is clinically important. Finally, a combination of the same single compartment lung model and the hysteresis loop analysis (HLA) method predicted airway pressure, but only at the highest PEEP in a recruitment maneuver, given parameters identified from multiple prior low PEEP steps, which is not clinically effective.

Finally, it is important to note that while lung models are common, predictive lung models are extremely limited. Mathematical models at 1D cellular level, 2D tissue level and 3D geometry level have enabled a better understanding of lung physiology and mechanics. However, these models are complex, have many unknown parameters, can suffer overfitting issues as the models seek to minimise replication errors to validation data, and are thus not suitable for personalised prediction. Therefore, while models are common, personalised models are less common, and predictive personalised models are currently unavailable.

Hence, this invention addresses the above problems with an automated digital cloning method and personalized virtual patient model heretofore unknown in the art.

SUMMARY

In accordance with one aspect of the present invention, there is provided a method for guiding mechanical ventilation of a patient including the steps of:
a) measuring the clinical pressure, volume and flow data of the patient on a ventilator;
b) using nonlinear hysteresis analysis (HLA) to find compliances (1/stiffness values) and resistances for use in a nonlinear hysteresis loop model (HLM), including identifying the presence of asynchrony;
c) using an algorithm, or other method, to create a patient specific lung mechanics model every breath or at any reasonable clinical interval for the patient, including the ability to predict the evolution of compliance (1/stiffness) using the HLM or any similar relevant model, including the ability to reconstruct the pressure-volume (PV) loop waveforms unaltered by asynchrony of any type, including estimating asynchrony magnitude using this model;
d) predicting the pressure-volume (PV) loop response of the patient's lung to any changes in ventilator settings based on predicting the evolution of compliance;
e) adjusting mechanical ventilation (MV) mode or settings to optimize care to desired, e.g., clinically specified guidelines;
f) monitoring the patient; and
g) repeating steps a) through f) at any clinically relevant interval until a desired state of health is achieved.

In accordance with another aspect of the present disclosure, there is provided a device for controlling mechanical ventilation of a patient, including: a processor programmed to develop a hysteresis loop model based on measured PV loop and to use HLA to obtain in real-time lung mechanics parameters for forecasting individualized MV parameters; a memory; a data input; and a display.

These and other aspects of the present disclosure will become apparent upon a review of the following detailed description and the claims appended thereto.

DETAILED DESCRIPTION

Figure 1:
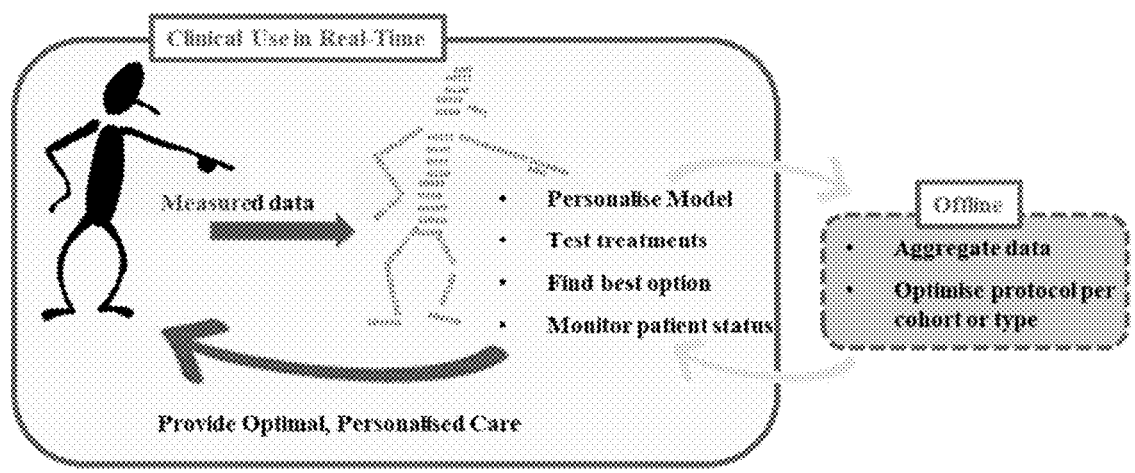
FIG. 1 shows how actual patient data is used to develop a digital clone based on a computer model to enable actual patient specific state and potential response to care.

Presented is a virtual patient or digital clone based on a computer or computational model of patient-specific lung physiology and mechanics capable of augmenting clinical data and enabling a more comprehensive picture of actual patient-specific state and potential response to care (FIG. 1). An accurate, predictive virtual patient enables more personalised, confident, and efficient design of MV care, minimising the risk of barotrauma and volutrauma. Personalised MV care could also reduce the length of MV (LoMV), which is critical for reducing cost and improving the capacity of health systems to provide adequate MV during the Covid-19 pandemic, as well as to improving outcomes.

Disclosed is a method for managing the mechanical ventilation of a patient which includes the following steps:
a) placing a patient on a mechanical ventilator;
b) measuring pressure, flow, and resulting volume of air delivered to the patient at any given ventilator setting and mode;
c) constructing a patient specific lung mechanics model based upon the patient's breathing in response to the delivered air pressure, flow, and resulting air volume;
d) predicting a pressure-volume (PV) loop and lung elastance values of the patient's lung in response to any possible changes in the ventilator settings or mode based on the patient specific lung mechanics model;
e) adjusting the mechanical ventilator settings to maintain the patient's response within a desired, e.g., clinically set safe, range of pressure, flow, and/or volume values;
f) monitoring changes to the patient's lung mechanics in real time; and
g) repeating steps d) through f) to maintain patient pressure, flow, and/or volume values within a desired, e.g., clinically set safe, range until the patient recovers and can be removed from the ventilator.

Further identifying the presence of asynchrony in a breath, as well as its magnitude, and compensating for the asynchrony in the response prediction by using additional modeling to reconstruct the patient's PV loop for that breath in step b) above which is unaffected by the asynchronous breathing effort that alters the measured pressure, flow, and volume delivered by the ventilator due to patient breathing effort.

Steps a)-g) above are similar for all forms of invasive MV modes and can be extended to non-invasive ventilation by adding a model for spontaneous breathing effort.

The present invention relates to an automated digital cloning method to create an accurate, predictive, and personalized virtual patient model enabling personalized precision MV care. A nonlinear hysteresis loop model (HLM) is proposed from the perspective of mechanical-physiological relevance for the dynamic respiratory system as the foundation computational model to capture essential nonlinear lung mechanics. The virtual patient model is created with the identified HLM model and prediction functions using clinical measurements at a low or given PEEP level. The additional lung volume retained during a change of PEEP, denoted $V_{frc}$, is clinically important and is also predicted using the virtual patient model. The current method includes personalized and patient-specific modeling of a mechanically ventilated patient which predicts the patient's lung mechanics and their response to changes in ventilation care in real-time.

In accordance with one aspect of the present invention, there is provided a method for guiding the mechanical ventilation of a patient including the steps of:
a) measuring the pressure and flow delivered to the patient by the ventilator, for example, either from the ventilator's sensors or from additional sensors added to the breathing circuit;
b) using nonlinear hysteresis analysis (HLA) to find compliances (1/stiffness values) and resistances for use in nonlinear hysteresis loop model (HLM), including identifying the presence of asynchrony;
c) using an algorithm, or other method, to create a patient specific lung mechanics model every breath or at any reasonable clinical interval for the patient, including the ability to predict the evolution of compliance (1/stiffness) using the HLM or any similar relevant model, including the ability to reconstruct the pressure-volume (PV) loop waveforms unaltered by asynchrony of any type to estimate asynchrony magnitude using this model;
d) predicting the pressure-volume (PV) loop response of the patient's lung to any changes in ventilator settings based on predicting the evolution of compliance;
e) adjusting mechanical ventilation (MV) mode or settings to optimize care to clinically specified guidelines;
f) monitoring the patient; and
g) repeating steps a) through f) at any clinically relevant interval until a desired state of health is achieved.

Figure 2:
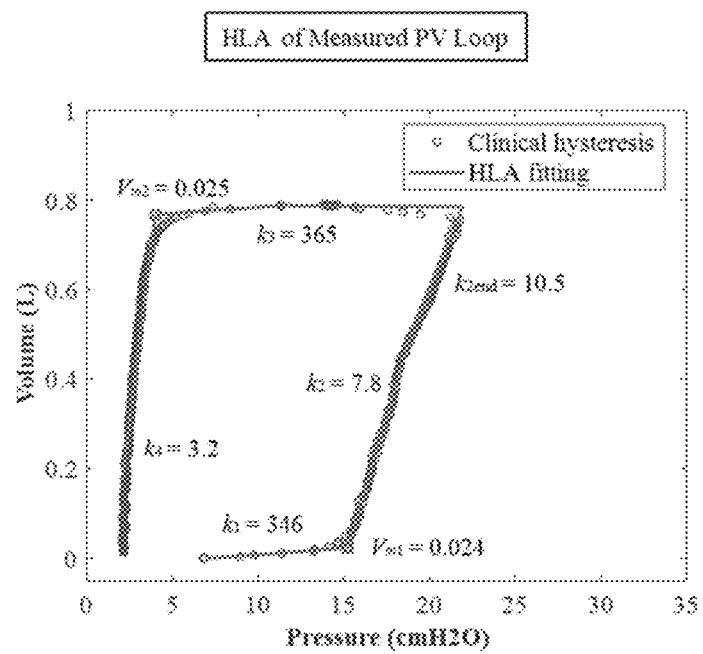
FIG. 2 shows a measured PV loop with HLA analysis.
Figure 3:
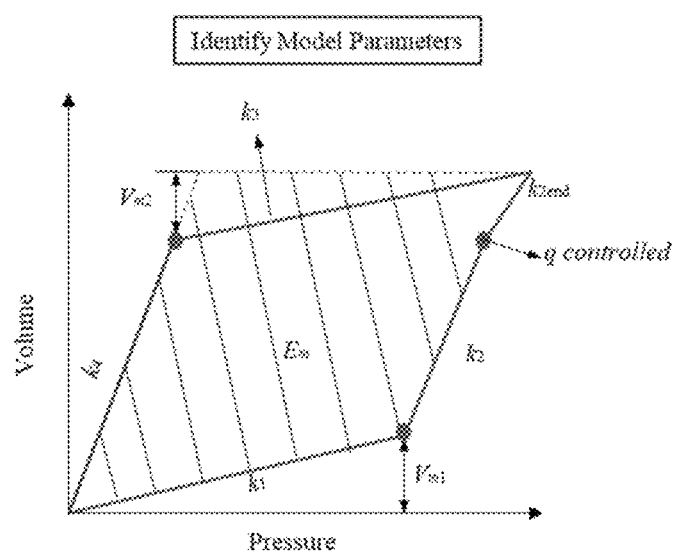
FIG. 3 shows identification of model parameters.

In an embodiment, the hysteresis loop analysis is based on clinical input data (FIG. 2). At any initial baseline PEEP (positive end-expiratory pressure), the hysteresis loop analysis method (HLA) is applied to identify elastance values for the whole breath. HLA separates the P-V loop for a breath into 5 segments, as shown in FIG. 3. For expiration, 2 segments are identified with two elastances, k3 and k4, respectively. For inspiration, the half cycle is first divided into two segments, k1 and k2. Subsequently the k2 segment is assessed to find a potential third segment, increased stiffness (reduced compliance) k2end, arising from any distension. K2end is reduced compliance at the end of expiration. K2end is used to capture possible over distension as PEEP rises. Over distension is minimized to avoid VILI (ventilator induced lung injury). Finally, a greater number of segments during inspiration and/or expiration can be used to identify the presence of asynchrony in the breathing effort, outside of normal mechanics and distension and its magnitude.

Next an HLM model is used with elastance evolution basis functions to predict parameters as a function of PEEP levels. This HLM model, or any similar relevant model, can also be used to reconstruct PV loops and waveforms unaltered by asynchrony, thus enabling identification of the underlying lung mechanics, as well as quantification of the magnitude of asynchrony as the area between the measured and reconstructed and unaltered PV loops, the differences in peak pressure and/or volume, or any similar metric of pressure, volume, flow, or energy difference in the work of breathing.

Figure 4:
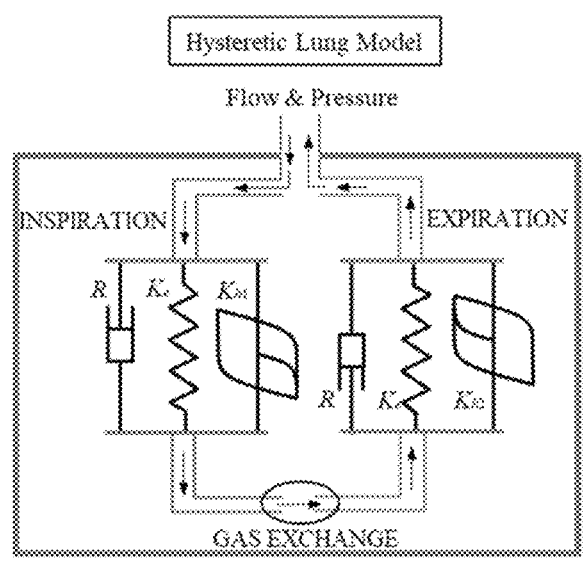
FIG. 4 shows a mechanical model of the lung.

A dynamic equation of motion for a relevant and effective HLM lung mechanics model is defined:

$$\ddot{V} = R\dot{V} + K_e V + K_{h1} V_{h1} + K_{h2} V_{h2} = f_V(t) + PEEP \quad (1)$$

where V is the volume of air delivered to the lungs, $V_{h1}$ and $V_{h2}$ are hysteretic volume response during inspiration and expiration, respectively, $K_e$ represents the alveolar recruitment elastance, named k2 in this approach, $K_{h1}$ and $K_{h2}$, are determined by two nonlinear hysteretic springs for alveolar hysteresis elastance during inspiration and expiration, respectively, R is the airway resistance, PEEP is the positive end-expiratory pressure, and $f_v(t)$ is the steady-state input force. This is shown in FIG. 4. Note other dynamic equations of motion for lung mechanics could be used.

Figure 5:
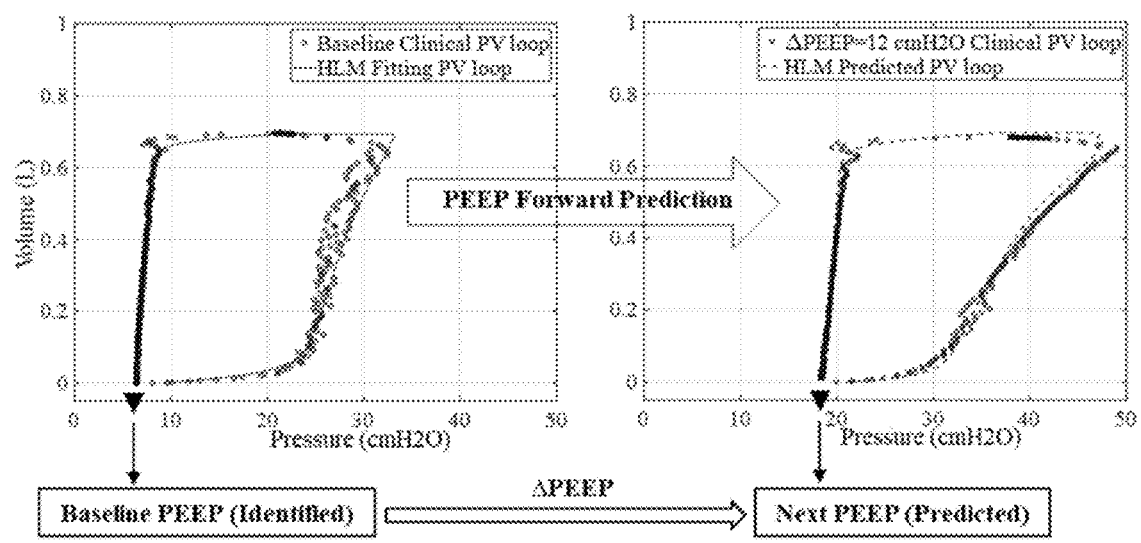
FIG. 5 shows actual versus prediction PV loop with change in PEEP.

The model developed with equation (1) is used to predict PV loop response of lung to changes in ventilator settings. Predicted PV loops can be examined to determine changes to minimize elastance and distension, while maximizing recruited lung volume and/or minimising risk of distension and VILI. Elastance (1/compliance) is the pressure required to inflate lungs per unit of lung inflation volume. Distension is swelling or stretching of alveoli or lung airways caused by excessive internal pressure. Recruited lung volume ($V_{frc}$) can be maximized while distension is minimized, where $V_{frc}$ and distension are both variables which can be used to guide MV in addition to minimising recruitment elastance and peak pressures. An example output of the model is shown in FIG. 5 where predicted and actual PV loops at 2 different PEEP levels are shown from clinical data. The excellent agreement confirms that predicted PV loops can be used as basis for changes in PEEP, or other MV settings, that allow personalized patient care.

Figure 6:
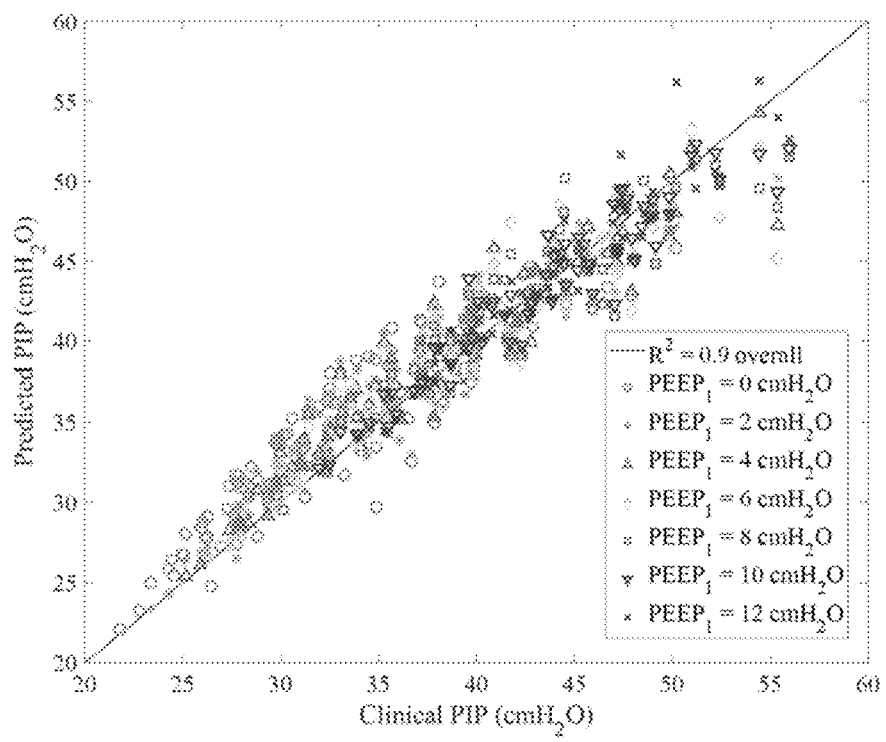
FIG. 6 shows predicted vs and actual data for patient PIP.

A measure of prediction accuracy can be seen in FIG. 6 where PIP (peak inspiratory pressure) data from 32 clinical patients is plotted versus PIP calculated from the HLM model shows settings with good agreement. Control of PIP is important to minimize risk of barotrauma. Similar plots are found for other clinical parameters and lung responses.

Figure 7:
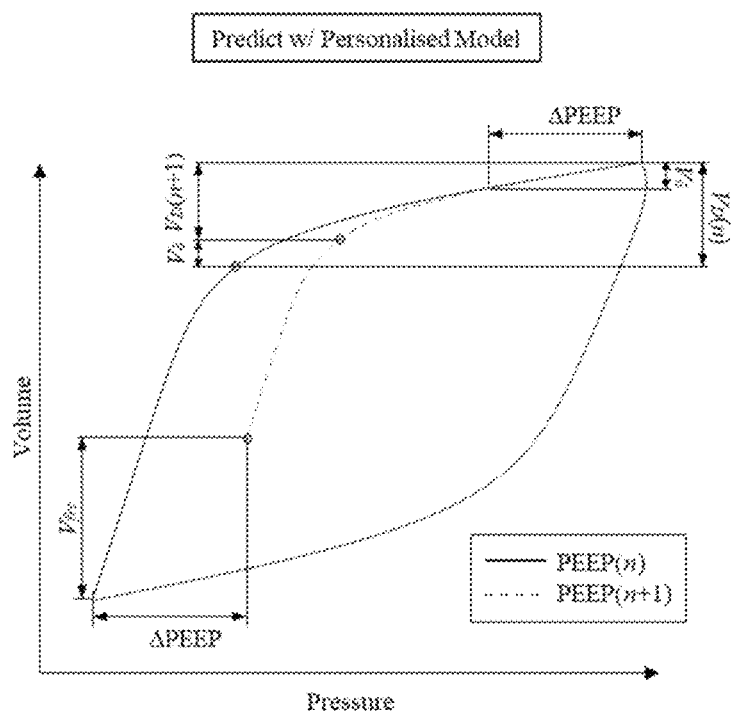
FIG. 7 shows prediction of $V_{frc}$ recruited lung volume with change in PEEP.

In particular, FIG. 7 shows calculated prediction of $V_{frc}$ recruited lung volume with change in PEEP. Increasing recruited volume is imperative so that the patient can be removed from mechanical ventilation. $V_{frc}$ can currently only be obtained by invasive procedures and imaging, such as CT scans.

The model allows the clinician to make adjustments to settings to optimize care while minimizing any harm to the patient by predicting lung response and outcomes before changing settings, which reduces risk of unintended VILI or harm. The overall goal is to personalise and optimise care with the desired result of decreasing time on mechanical ventilation and improving patient outcomes, where decreased time of MV has been shown to result in decreased patient mortality.

Figure 8:
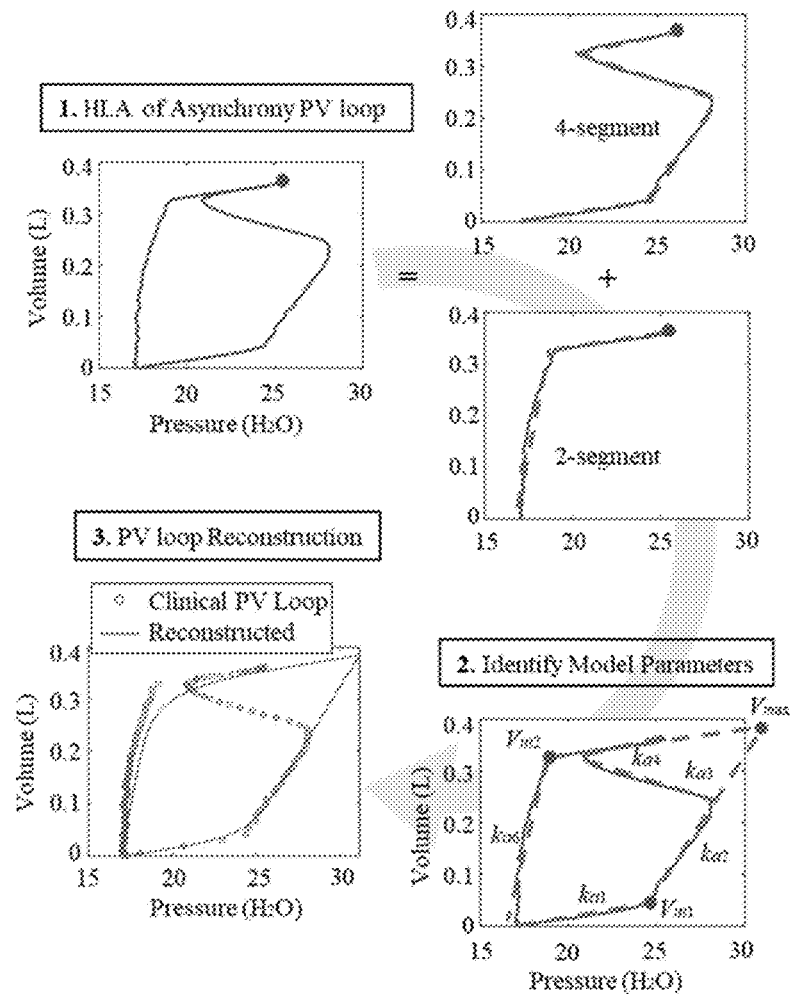
FIG. 8 shows PV loop reconstruction with asynchrony.
Figure 9:
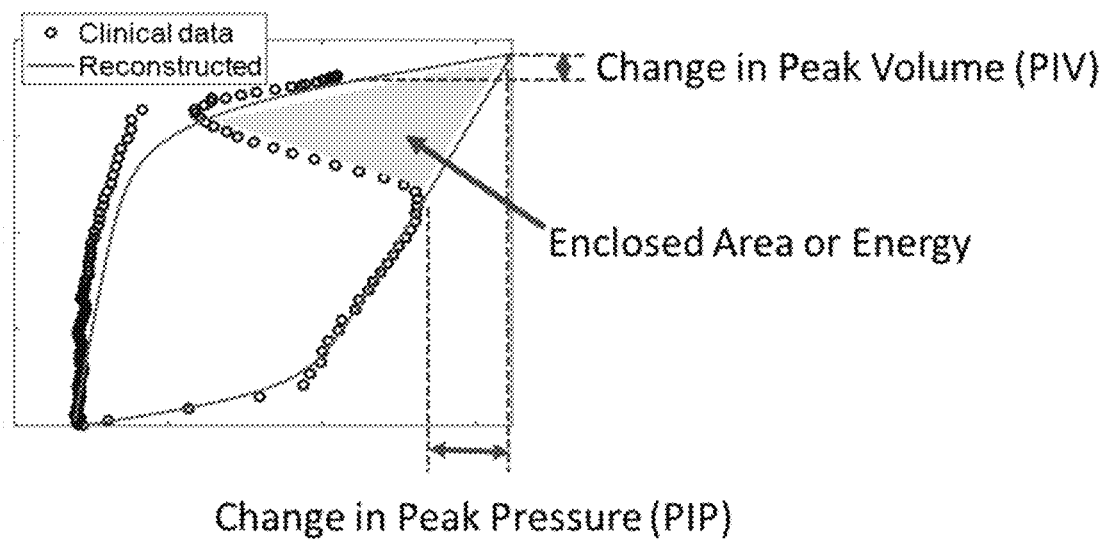
FIG. 9 shows PV loop with and without reconstruction with 3 possible metrics for asynchrony magnitude.

The automated digital cloning method creates an accurate, predictive, and personalized virtual patient model enabling personalized precision MV care. A nonlinear hysteresis loop model (HLM) is proposed from the perspective of mechanical-physiological relevance for the dynamic respiratory system as the foundation computational model to capture essential nonlinear lung mechanics. The virtual patient model is created with the identified HLM model and prediction functions using clinical measurements at any given PEEP level. It can also be used to identify the incidence or presence of asynchrony, the type of asynchrony, and its magnitude by identifying additional HLA segments, as shown in FIG. 8, where the results can be used to identify a HLM model and PV loop unaffected by the asynchrony so asynchrony magnitude may be calculated based on changes in work of breathing, energy, or/and peak pressures, volumes, and flows, as shown in FIG. 9. None of these capabilities or results are possible with today's systems or ventilators. Finally, the additional lung volume retained during a change of PEEP, denoted $V_{frc}$, and the potential or actual existence of distension are clinically important and are also predicted using the virtual patient model, neither of which is currently possible with existing models, methods, ventilators, or systems without added invasive procedures or measurements.

Figure 10:
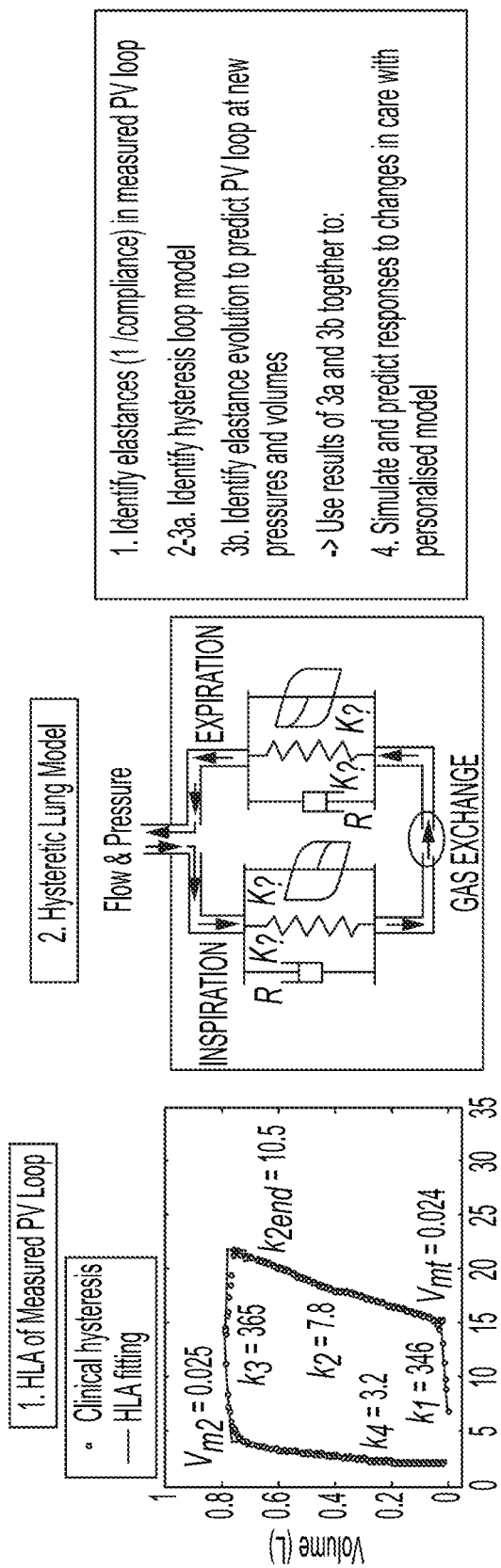
FIG. 10 shows how the PV loop data is used to identify the HLM model parameters and predict a new PV loop at different PEEP and/or other changed MV settings.
Figure 10:
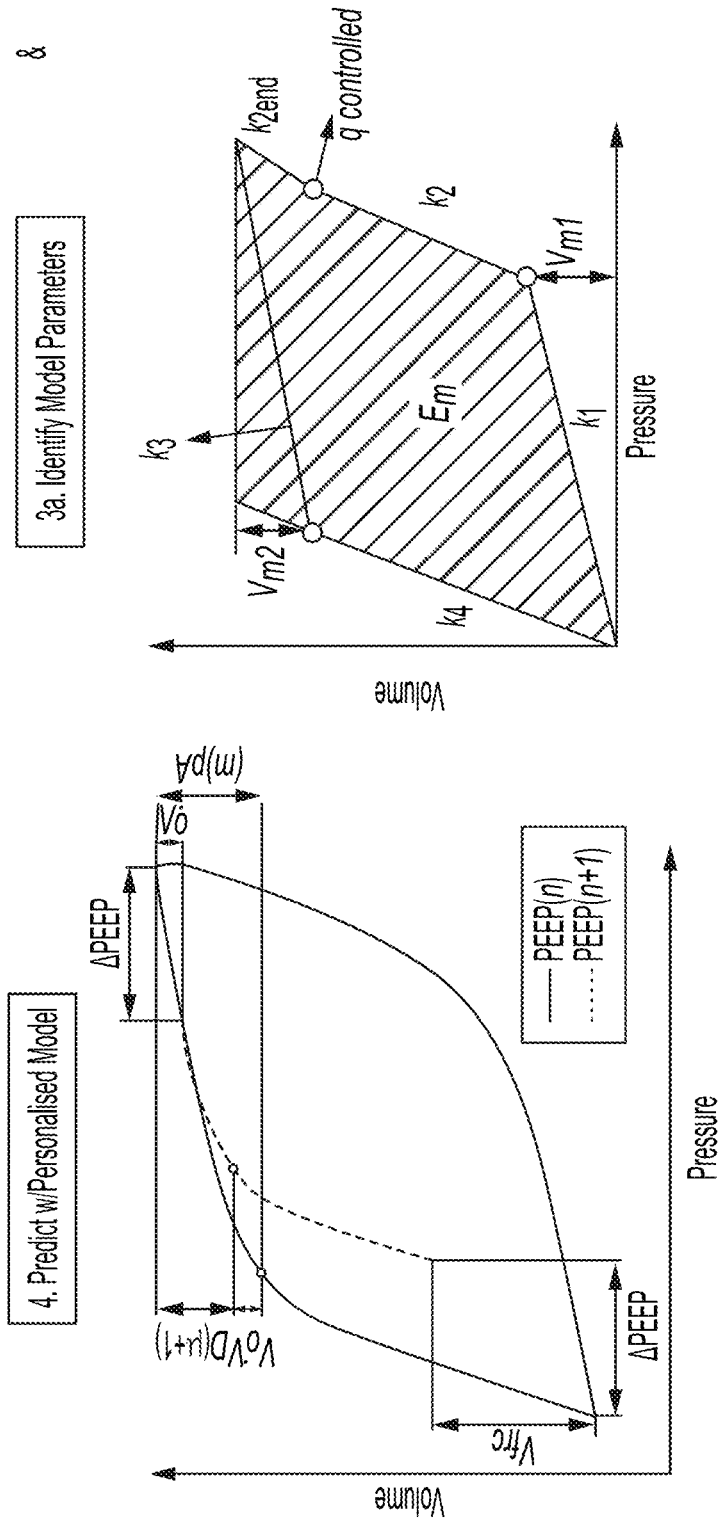
Figure 10:
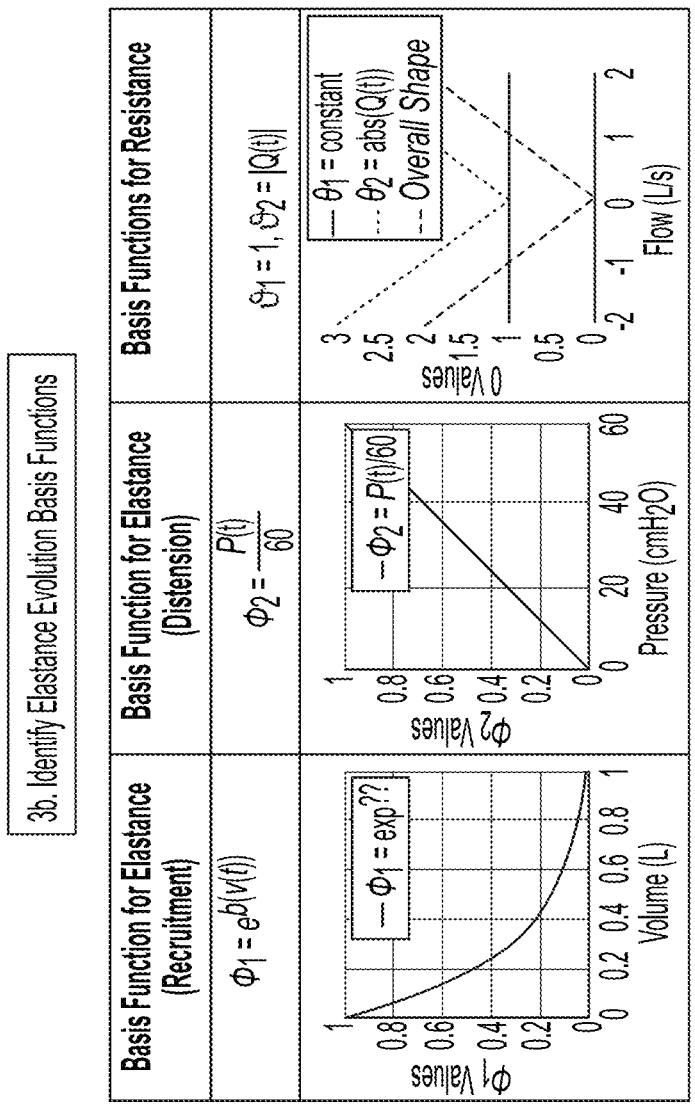

Given the values of lung stiffness and the HLM model, the PV loop and $V_{frc}$ can be predicted for any change in ventilator settings (pressures and/or flows and volumes delivered). These predictions can be used to adjust PEEP or pressure and flow inputs delivered to the patient to provide safer care, such as ventilating the patient at the PEEP associated with minimum lung elastance, and/or maximizing $V_{frc}$, and/or minimizing peak inspiratory pressures or volumes to safe levels to minimise risk of ventilator induced lung injury (VILI), among many possibilities. FIG. 10 combines FIGS. 2-4 and FIG. 7 to provide a complete process flow chart.

The disclosure will be further illustrated with reference to the following specific examples. It is understood that these examples are given by way of illustration and are not meant to limit the disclosure or the claims to follow.

Figure 11:
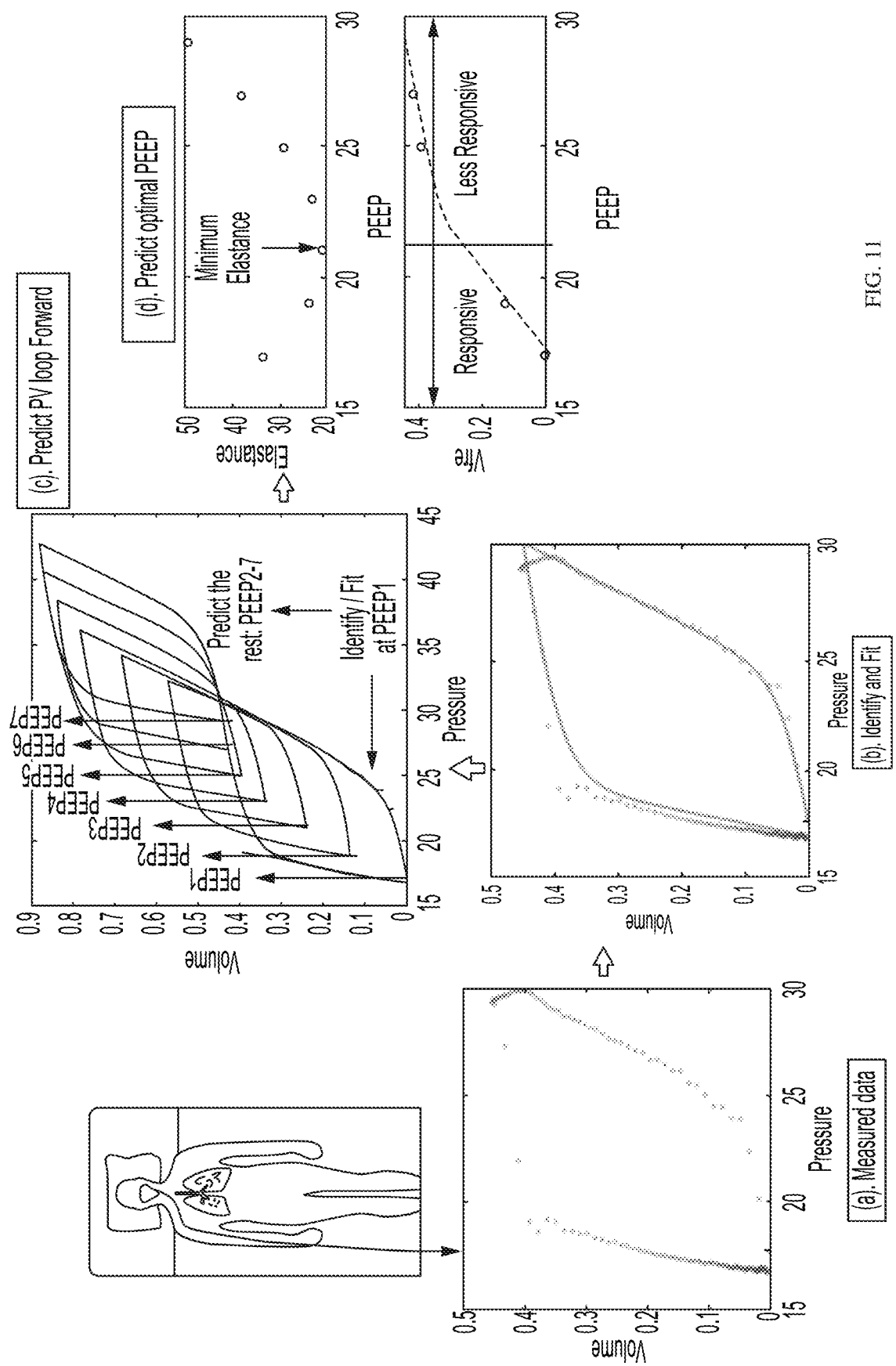
FIG. 11 shows an example of how this model and prediction capability can be used to guide MV care, in this case, in terms of minimizing lung stiffness (or elastance) and/or $V_{frc}$ responsiveness due to changes in PEEP.

Example 1: measured pressure and flow data of patient breathing were used to construct the PV loop at the baseline PEEP as PEEP1, as shown in FIG. 11(a). Next, the HLA identification was implemented to fit the measured PV loop at PEEP1, as shown in FIG. 11(b) and to create the HLM model per FIG. 10. PV loops at higher PEEP settings from PEEP2 to PEEP7 were then predicted based on the basis functions and HLM modelling, as shown in FIG. 11(c). Finally, the evolution curve of lung elastance and $V_{frc}$ responding to the changes of PEEP from PEEP1 to PEEP7 are predicted to find the PEEP level from PEEP1 to PEEP7 associated with the minimum elastance and maximum responsive of $V_{frc}$, indicating the best PEEP value or range for clinical use, as shown in FIG. 11(d).

Figure 12:
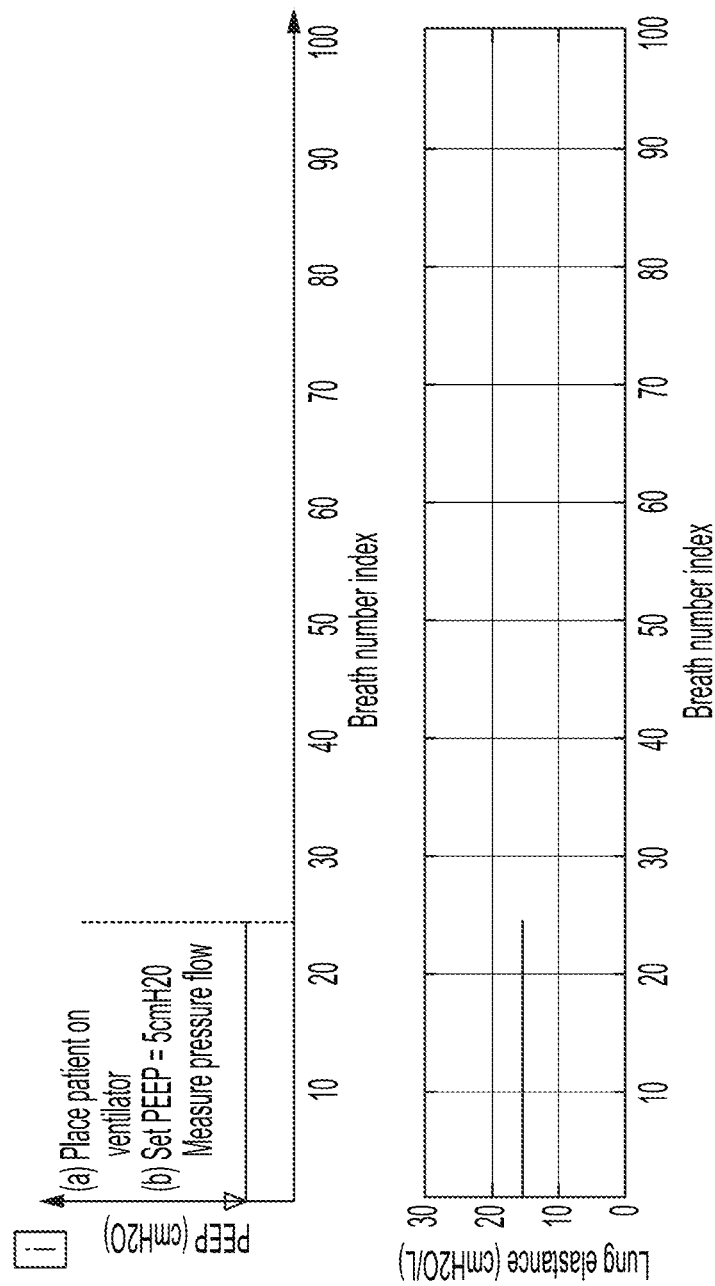
FIG. 12 shows an example of how this model and predication capability could be used to select a PEEP for minimum patient-specific elastance.
Figure 12:
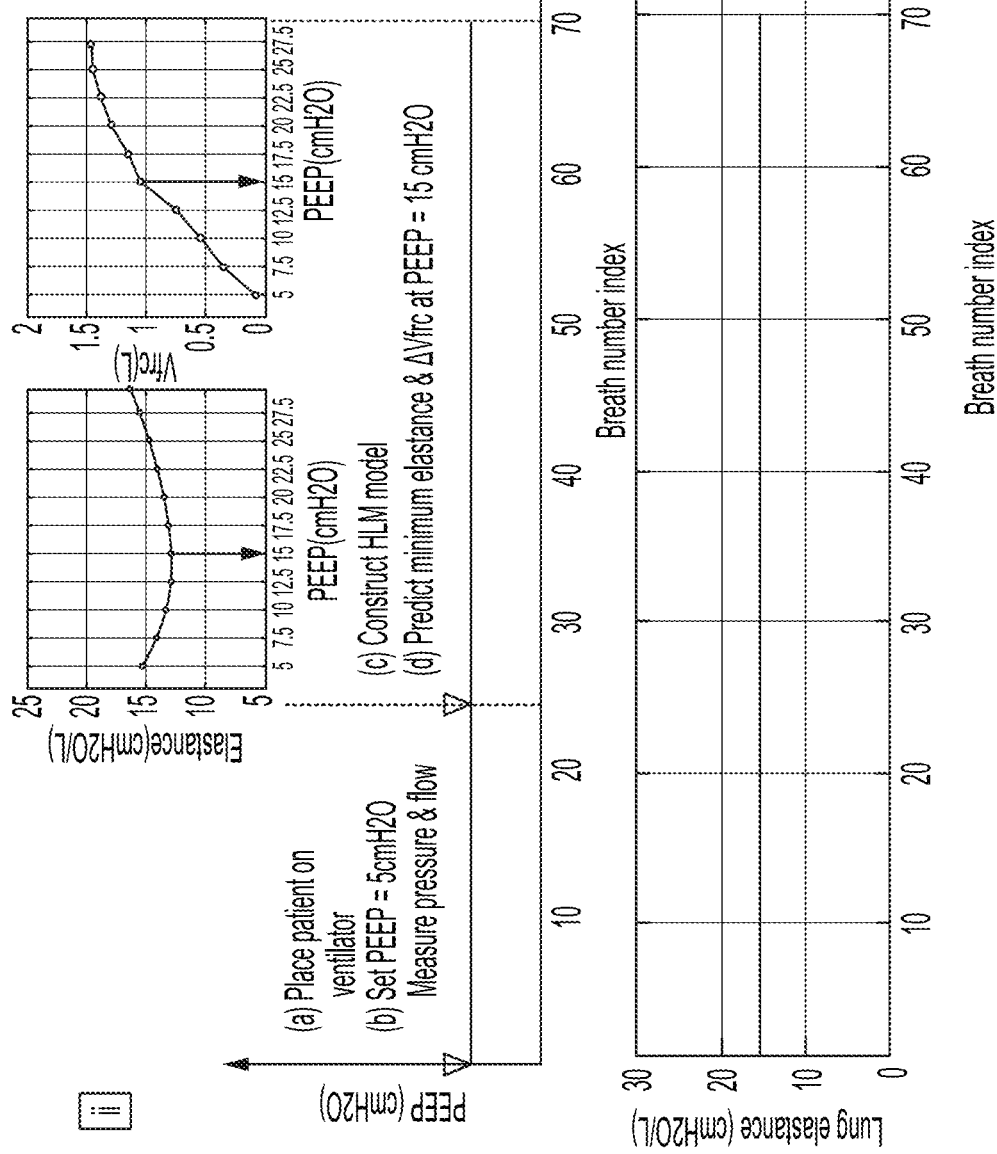
Figure 12:
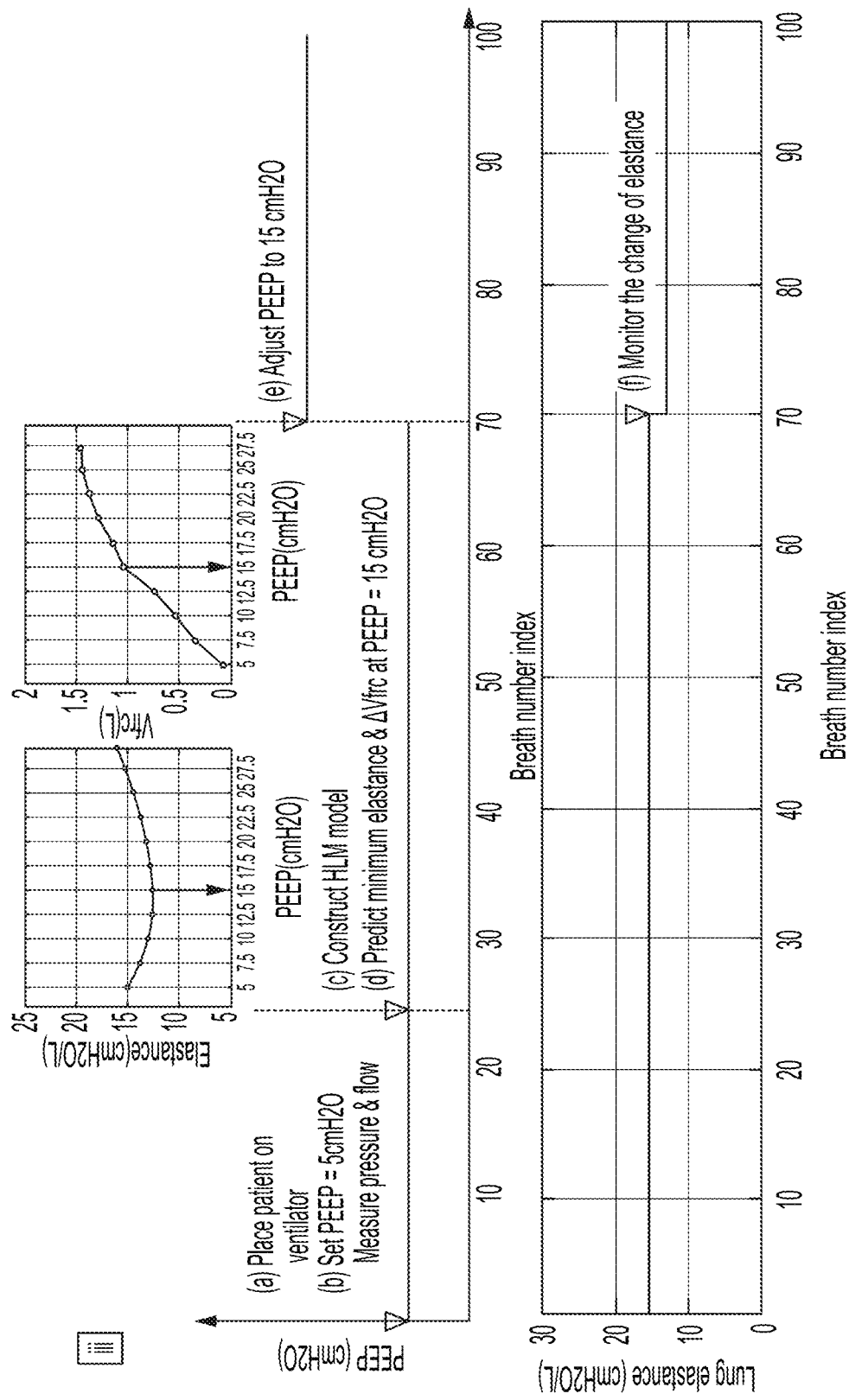

Example 2: as shown in FIG. 12, follows the steps a)-f) disclosed in the method for managing the mechanical ventilation of a patient. If asynchrony were to occur the 3 steps in FIG. 8 would be used to reconstruct a PV loop unaffected by the asynchronous breathing effort for use in creating a lung mechanics model for steps b) and c) in FIG. 12.

Although various embodiments have been depicted and described in detail herein, it will be apparent to those skilled in the relevant art that various modifications, additions, substitutions, and the like can be made without departing from the spirit of the disclosure and these are therefore considered to be within the scope of the disclosure as defined in the claims which follow.

What is claimed:

1. A method for managing a mechanical ventilation of a patient, comprising the following steps:
   a) placing the patient on a mechanical ventilator;
   b) measuring pressure, flow, and resulting volume of air delivered to the patient at a given ventilator setting and mode;
   c) constructing a patient specific lung mechanics model based upon the patient's breathing in response to the delivered air pressure, flow, and resulting volume;
   d) predicting a pressure-volume (PV) loop and lung elastance values of the patient's lung in response to changes in the given ventilator settings or mode based on the patient specific lung mechanics model;
   e) adjusting settings of the mechanical ventilator to maintain the patient's response within a desired range of one or more of pressure, flow, and volume values;
   f) monitoring changes to the patient's lung mechanics in real time; and
   g) repeating steps d) through f) to maintain the one or more of patient pressure, flow, and volume values within the desired range until the patient can be removed from the mechanical ventilator.

2. The method claim 1, further comprising predicting a retained or lost end expiratory volume ($V_{frc}$) when a positive end expiratory pressure (PEEP) is increased or decreased.

3. The method of claim 1, further comprising predicting distension of the patient's lungs using a value of k2end, wherein k2end is reduced compliance at the end of expiration.

4. The method of claim 1, further comprising collecting and aggregating data over time, to optimize models, methods and/or protocols.

5. The method of claim 2, where the retained volume $V_{frc}$ or the lost end expiratory volume $V_{frc}$ as positive end expiratory pressure (PEEP) is used to determine ventilation care choices in whole or in part with other predicted or clinical variables.

6. The method of claim 3, where predicted values of the distension and the k2end are used to determine ventilation care choices in whole or in part with other predicted or clinical variables.

7. The method of claim 2, where predicted distension, k2end and/or the $V_{frc}$ are used to determine ventilation care choices in whole or in part with other predicted or clinical variables.

8. The method of claim 1, further comprising estimating and reconstructing with additional modeling the PV loop unaffected by asynchrony.

9. The method of claim 8, where the reconstructed PV loop is compared to the initial PV loop to estimate an asynchrony magnitude.

10. The method of claim 8, further comprising compensating for the asynchrony when adjusting the mechanical ventilator settings.

11. A device for controlling mechanical ventilation of a patient, comprising:
    a mechanical ventilator and sensors for measuring pressure, flow, and resulting volume of air delivered to the patient on the mechanical ventilator at a given ventilator setting and mode; and
    a processor programmed to
      a) construct a patient specific lung mechanics model based upon the patient's breathing in response to the delivered air pressure, flow, and resulting volume;
      b) predict a pressure-volume (PV) loop and lung elastance values of the patient's lung in response to changes in the given ventilator settings or mode based on the patient specific lung mechanics model;
      c) adjust the mechanical ventilator settings to maintain the patient's response within a desired range of one or more of pressure, flow, and volume values;
      d) monitor changes to the patient's lung mechanics in real time; and
      e) repeat steps b) through d) to maintain the one or more of patient pressure, flow, and volume values within the desired range until the patient can be removed from the mechanical ventilator; and
    develop the personalized lung mechanics model to forecast individualized mechanical ventilator parameters configured to obtain real-time lung mechanics parameters based on the personalized lung mechanics model;
    a memory; a data input; and a display.

12. The device of claim 11, wherein the personalized lung mechanics model incorporates a nonlinear hysteresis loop analysis.

13. The device of claim 11, wherein the personalized lung mechanics model includes a measured PV loop.

* * * * *